United States Patent
Grooters

(10) Patent No.: US 6,387,087 B1
(45) Date of Patent: *May 14, 2002

(54) AORTIC CANNULA

(76) Inventor: Ronald K. Grooters, 909 28th St., West Des Moines, IA (US) 50265

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 656 days.

(21) Appl. No.: 08/763,728

(22) Filed: Dec. 11, 1996

(51) Int. Cl.[7] .............................................. A61M 31/00
(52) U.S. Cl. ........................ 604/507; 604/537; 604/264
(58) Field of Search ............................. 604/4, 264, 93, 604/280, 53, 52, 30, 39, 273–275, 28, 93.01, 523, 500, 507, 508, 537

(56) References Cited

U.S. PATENT DOCUMENTS

| 191,879 A | | 6/1877 | Pfarre | |
|---|---|---|---|---|
| 4,198,984 A | | 4/1980 | Taylor | 128/349 |
| 4,276,880 A | * | 7/1981 | Malmia | 128/221 |
| 4,361,152 A | | 11/1982 | Patel | 604/99 |
| 4,643,712 A | | 2/1987 | Kulik et al. | 604/4 |
| 4,795,446 A | * | 1/1989 | Fecht | 604/264 |
| 4,863,441 A | | 9/1989 | Lindsay et al. | 604/280 |
| 5,147,334 A | * | 9/1992 | Moss | 604/264 |
| 5,259,371 A | * | 11/1993 | Tonrey | 128/200.26 |
| 5,320,599 A | * | 6/1994 | Griep et al. | 604/35 |
| 5,344,412 A | | 9/1994 | Wendell et al. | 604/280 |
| 5,354,288 A | | 10/1994 | Cosgrove et al. | 604/264 |
| 5,360,414 A | | 11/1994 | Yarger | 604/264 |
| 5,407,441 A | * | 4/1995 | Greenbaum | 604/280 |
| 5,451,216 A | | 9/1995 | Quinn | 604/270 |
| 5,480,392 A | | 1/1996 | Mous | 604/280 |
| 5,616,137 A | * | 4/1997 | Lindsay | 604/264 |
| 5,643,226 A | * | 7/1997 | Cosgrove et al. | 604/264 |

* cited by examiner

Primary Examiner—Brian L. Casler
Assistant Examiner—Cris L. Rodriguez
(74) Attorney, Agent, or Firm—McKee, Voorhees & Sease, P.L.C.

(57) ABSTRACT

An improved aortic cannula for use in heart bypass surgery comprises an elongated tube with a terminal end. The improvement relates to the provision of two large openings adjacent the terminal end of the cannula, and an inverted cup at the terminal end to redirect the flow of blood as the blood exits through the discharge openings. The cup deflects a portion of the blood rearwardly so as to slow the velocity of the blood. The openings and the cup serve to reverse the flow of blood toward the ascending aorta and away from the aortic arch so as to prevent dislodging plaque, and thereby decreasing the chances of stroke.

2 Claims, 2 Drawing Sheets

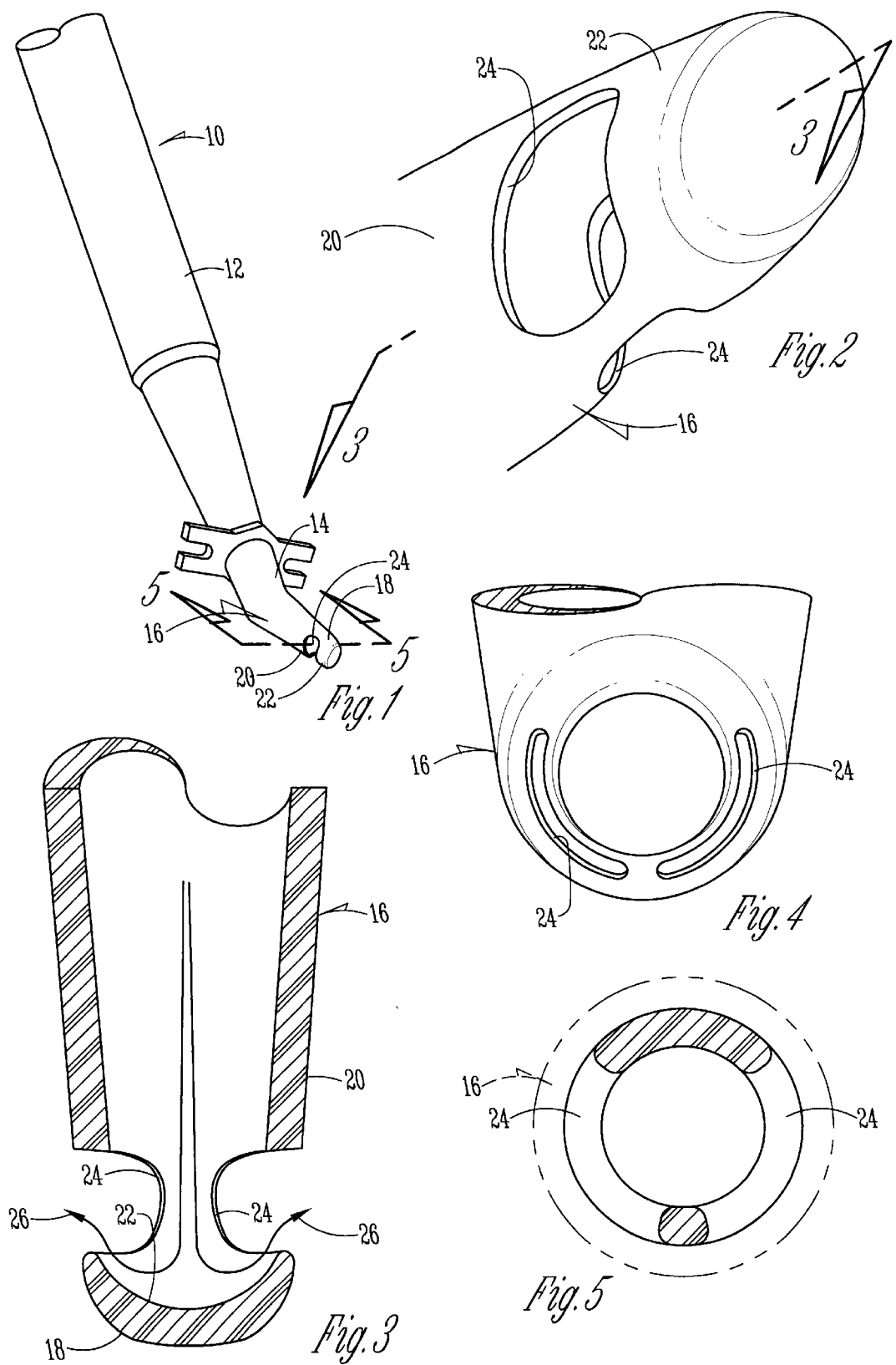

AORTIC CANNULA

BACKGROUND OF THE INVENTION

The present invention relates generally to medical devices and, in particular, aortic cannulas. Aortic cannulas are used to return blood to the aorta while the heart is by-passed during heart surgery. These cannulas are purposely made with small diameters to minimize the disruption to the aorta, which in many heart surgery patients have advanced complex atherosclerotic plaque with adherent blood thrombi.

Aortic cannulas generally comprise an elongated tube having a terminal end. In at least some styles of conventional cannulas, a single opening is provided in the terminal end which provides a single stream of blood exiting the cannula and entering the aortic arch. Due to the small diameter of the cannula, the flow velocity of the blood through the single opening in the terminal end of the cannula is extremely high, resulting in "jet" flow. The fluid pressure at the discharge end of the prior art cannula is also high. It is believed that the force of this jet stream of blood dislodges atherosclerotic plaque and/or adherent thrombi from the walls of the aorta, causing embolisms and strokes.

Attempts in the art to prevent embolisms resulting from cannulation have included designing the cannula in order to reduce the velocity of blood exiting the terminal end. For instance, U.S. Pat. No. 5,354,288 describes a cannula having a conical diffuser placed toward the proximal end of the cannula. The cannula includes several outlet openings in the sidewall to permit blood deflected by the diffuser to flow out of the cannula. This cannula design, however, still directs blood toward the sides of the aortic arch wherein the atherosclerotic plaque usually lies. Thus, the patient is still susceptible to embolisms and strokes.

Therefore, a primary objective of the present invention is the provision of an aortic cannula which does not cause injury to the aortic tissues or dislodge atherosclerotic plaque during cannulation.

Another objective of the present invention is the provision of an aortic cannula which reduces the velocity of the blood exiting the cannula.

A further objective of the present invention is the provision of an aortic cannula which reduces the risk of embolisms or stroke present with the use of conventional cannulas.

Yet another objective of the present invention is the provision of a aortic cannula which is economical to manufacture and convenient, durable, and safe to use.

These and other objectives will be apparent from the following description of the invention.

SUMMARY OF THE INVENTION

The improved aortic cannula of the present invention includes an elongated tube having a terminal end. The improvement comprises two large openings adjacent the terminal end of the cannula as well as an inverted cup at the terminal end of the cannula. The openings at the terminal end reduce the velocity of the exiting blood and the inverted cup redirects the flow of blood as it exits through the discharge openings. The blood jet exits in a rearward direction towards the ascending aorta, and away from the aortic arch, which often contains atherosclerotic plaque. Thus, the risk of stroke from dislodged plaque is significantly reduced.

DESCRIPTION OF THE DRAWINGS

FIG. 1 is a perspective view of the aortic cannula of the present invention.

FIG. 2 is a perspective view of the bottom of the aortic cannula shown along lines 2—2 of FIG. 1.

FIG. 3 is a sectional view of the aortic cannula taken along lines 3—3 of FIG. 2.

FIG. 4 is a front side elevational view of the aortic cannula through the terminal end.

FIG. 5 is a cross sectional view of the aortic cannula through the elongated tube opposite the terminal end taken along lines 5—5 of FIG. 1.

DETAILED DESCRIPTION OF THE PREFERRED EMBODIMENT

Figure 6:
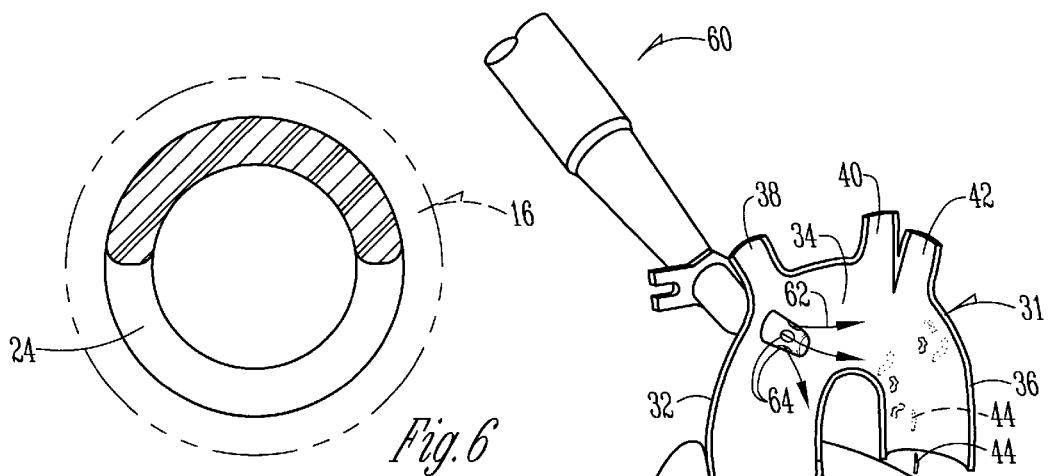
FIG. 6 is a bottom side elevational view of an alternative embodiment of the aortic cannula.

The aortic cannula of the present invention is generally designated in the drawings by the reference numeral 10. The aortic cannula includes an elongated tube 12 having a terminal end 16 with a lumen 14 extending therebetween. The terminal end 16 includes a forward surface 18 and a rearward surface 20. The aortic cannula further includes an inverted cup 22 at the terminal end 16. Adjacent the terminal end 16 of the cannula 10 are two large openings 24 radially spaced adjacent the rearward surface 20 of the terminal end 16.

The cannula 10 tapers toward the terminal end 16 so that the terminal end 16 has a diameter of between about 6 mm and 8 mm, to fit in the aorta of the patient. As shown in FIG. 1, the inverted cup 22 on the terminal end 16 of the cannula 10 is angled to direct the flow of the blood from the cannula 10 rearward as the blood exits through the openings 24. Thus, the velocity of the blood is substantially reduced. The inverted cup 22 preferably has an apex angle of between about 10° to about 45° to diffuse the flow of blood away from the aortic arch and toward the ascending aorta. The inverted cup 22 is preferably molded in one piece with the cannula 10. The inverted cup 22 also facilitates the insertion of the cannula 10 into the aorta and further reduces the likelihood of damage to the aorta once the terminal end 16 of the cannula 10 is place in the aorta.

The two large openings 24 preferably are elongated in shape and closely spaced on the rearward surface 20 of the terminal end 16. The openings 24 should be of a size large enough to reduce the velocity of blood exiting the cannula 10. While there are preferably two openings 24, in an alternative embodiment of the invention as shown in FIG. 6, there is only one large opening 24 centered in the rearward surface 20 of the terminal end 16. It is also contemplated that more than two openings 24 could be used in the rearward surface of the terminal end 16.

As blood flows through the cannula 10 and reaches the terminal end 16, it is forced through openings 24 which reduce the velocity of the blood because of the change in blood flow direction and the greater area of the openings 24 in comparison to the conventional cannula wherein the blood exits through a single opening at the terminal end or a plurality of small diameter openings. The cup 22 in the terminal end 16 directs the blood to exit the cannula 10 rearwardly as shown by arrows 26, thus directing the blood away from the aortic arch and toward the ascending aorta.

Figure 9:
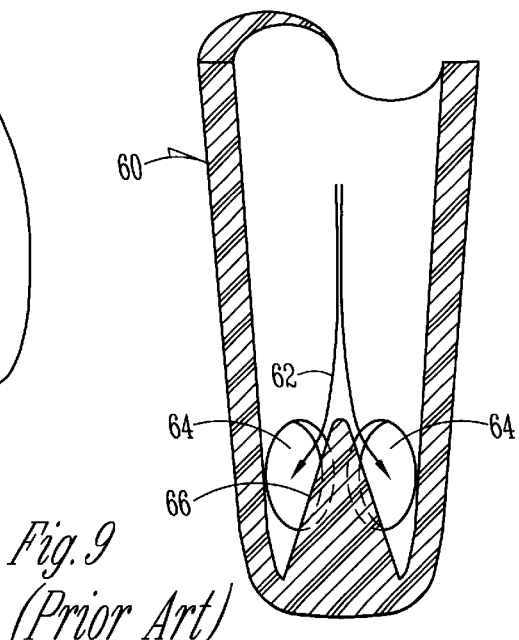
FIG. 9 is a sectional view of a prior art aortic cannula.

In comparison to the aortic cannula of the present invention, one type of prior art cannula 60, as shown in FIG. 9, also generally includes an elongated tube with a terminal end. Adjacent the terminal end are four equally radially disposed elongated slots 64. An inverted cone 66 resides at the tip to disperse blood into four streams for discharge through the openings. The blood therefore squirts in all directions from the cannula 60 and a substantial portion of the blood hits the aortic arch where there are often atherosclerotic plaques that can become dislodged. This is in contrast to the present invention wherein the blood flow is directed away from the atherosclerotic lesions in the aortic arch and is directed rearwardly to the ascending aorta.

Figure 7:
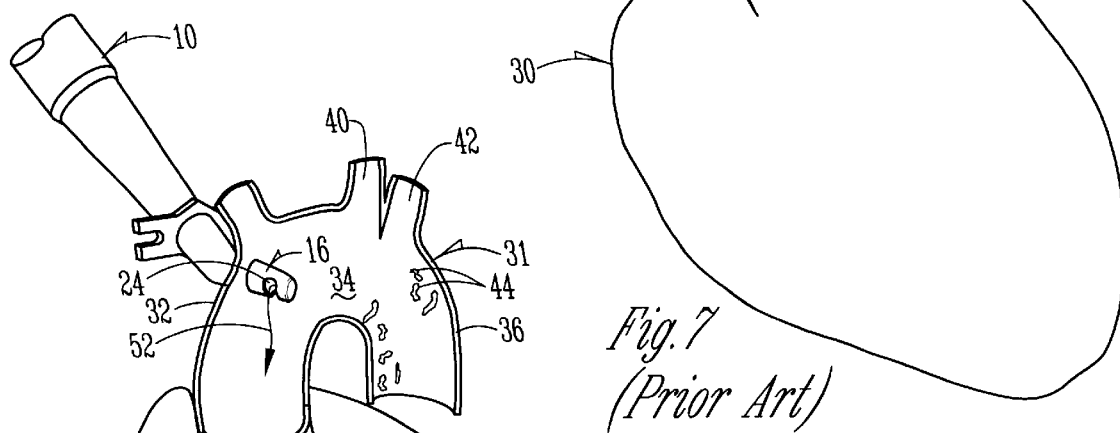
FIG. 7 is a schematic diagram of the heart and its primary blood vessels with reference to a prior art aortic cannula.
Figure 8:
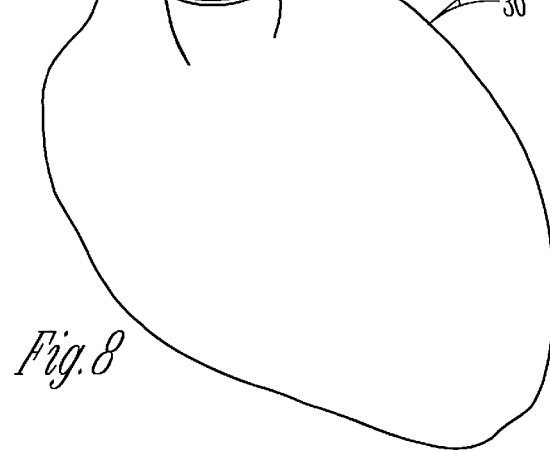
FIG. 8 is a schematic diagram of the heart and its primary blood vessels with reference to the aortic cannula of the present invention.

FIGS. 7 and 8 compare the aortic cannula of the present invention to a prior art cannula in operation. The heart 30 is shown along with the main blood vessels affected by cannulation. The aorta 31 is the main vessel leaving the heart 30. The aorta 31 is shown in three main sections which include the ascending aorta 32, the transverse aortic arch 34, and the descending aorta 36. The transverse aortic arch 34 is the primary area where atherosclerotic debris can be found in bypass patients. Branching from the aorta 31 are three large arteries: the innominate artery 38, the left carotid 40, and the left subclavian 42.

During bypass surgery, when a prior art cannula 60 is inserted in the aorta 31 as shown in FIG. 7, the blood exiting the cannula 60 is ejected in all directions as shown by arrows 62. A substantial portion of the blood contacts the transverse aortic arch 34 where the force of the blood can dislodge atherosclerotic plaques 44 which may be present. These plaques 44 then enter the bloodstream and may ultimately cause a stroke.

In contrast, when the aortic cannula of the present invention 10 is inserted into the aorta 31 as shown in FIG. 8, the blood exiting the cannula 10 is directed rearwardly in the direction of the ascending aorta 32, as indicated by arrow 52 and away from the transverse aortic arch 34 and the atherosclerotic plaques 44. The aortic cannula 10 of the present invention therefore reduces the chance that these plaques 44 will become dislodged during cardiac bypass surgery and, thus, ultimately helps to reduce the risk of embolism and strokes.

The aortic cannula 10 of the present invention thus reduces the velocity of blood exiting the cannula through the use of the openings 24 on the rearward surface 20 of the terminal end 16. Since the openings are placed on the rearward surface 20 only, rather than ejecting in all directions, the blood exits the cannula 10 rearwardly only and away from the aortic arch 34. Further, the inverted cup 22 at the terminal end 16 angles the flow of blood rearwardly as a further measure to prevent blood from directly contacting the aortic arch 34. Instead, the blood exits the cannula 10 and is directed toward the ascending aorta 32 where there is less chance of atherosclerotic lesions 44 being present.

The invention has been shown and described above in connection with the preferred embodiment, and it is understood that many modifications, substitutions, and additions may be made which are within the intended broad scope of the invention. From the foregoing, it can be seen that the present invention accomplishes at least all of the stated objectives.

What is claimed is:

1. A method of providing blood to the aorta of a patient, the method comprising the steps of:

making an opening in the aorta of the patient;

inserting a cannula through the opening into the aorta, the cannula having an elongated tube with a terminal end having forward and rearward surfaces, at least one opening in the rearward surface, and a cup at the terminal end to deflect blood rearwardly; and initiating blood flow through the cannula;

deflecting the blood flow with the cup for exit through the opening in the rearward surface and in the direction of the ascending aorta, and preventing blood flow from the cannula in the direction of the aortic arch.

2. A method of cannulization for heart by-pass surgery comprising:

making an incision in the aorta of a patient;

inserting a cannula into the incision, the cannula having a terminal end with an opening therein positioned within the aorta;

orienting the opening in the terminal end away from the aortic arch such that blood from the cannula is directed only toward the ascending aorta.

\* \* \* \* \*